(12) United States Patent
Darbe et al.

(10) Patent No.: US 8,794,078 B2
(45) Date of Patent: Aug. 5, 2014

(54) CEMENT TESTING

(75) Inventors: Robert Phillip Darbe, Tomball, TX (US); David Leon Meadows, Marlow, OK (US); Walmy Cuello Jimenez, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 139 days.

(21) Appl. No.: 13/542,011

(22) Filed: Jul. 5, 2012

(65) Prior Publication Data

US 2014/0007695 A1    Jan. 9, 2014

(51) Int. Cl.
*G01N 3/00*    (2006.01)

(52) U.S. Cl.
USPC .............................................. 73/803; 73/841

(58) Field of Classification Search
CPC .............. G01N 2203/0058; G01N 2203/0075; G01N 2203/0092; G01N 1/00
USPC .......................................... 73/760, 803, 841
See application file for complete search history.

(56) References Cited

U.S. PATENT DOCUMENTS

| | | |
|---|---|---|
| 2,662,827 A | 12/1953 | Clark |
| 3,541,845 A | 11/1970 | Kierkegaard-Hansen |
| 3,574,281 A | 4/1971 | Casey et al. |
| 3,619,463 A | 11/1971 | Budin et al. |
| 3,779,085 A | 12/1973 | Rice |
| 4,138,892 A | 2/1979 | Davis |
| 4,182,191 A * | 1/1980 | Ikeda ............................ 73/803 |
| 4,259,868 A | 4/1981 | Rao et al. |
| 4,377,087 A | 3/1983 | Rodot |
| 4,389,896 A | 6/1983 | Babcock |
| 4,408,489 A | 10/1983 | Spangle |
| 4,430,889 A | 2/1984 | Sutton |
| 4,487,056 A | 12/1984 | Wiley |
| 4,491,017 A | 1/1985 | Iyler |
| 4,538,452 A | 9/1985 | Hrvojic |
| 4,567,759 A | 2/1986 | Ekstrom et al. |
| 4,567,765 A | 2/1986 | Rao et al. |
| 4,573,342 A | 3/1986 | Jones |
| 4,607,530 A | 8/1986 | Chow |
| 4,648,264 A | 3/1987 | Freese et al. |
| 4,685,092 A | 8/1987 | Dumont |
| 4,691,558 A | 9/1987 | Vinson et al. |
| 4,703,427 A | 10/1987 | Catala et al. |
| 4,757,479 A | 7/1988 | Masson et al. |
| 4,809,237 A | 2/1989 | Vogel et al. |

(Continued)

FOREIGN PATENT DOCUMENTS

DE    86 01 833    1/1987
EP    0 124 383 A1    11/1984

(Continued)

OTHER PUBLICATIONS

Authorized Officer Igor Cantalapiedra, PCT International Search Report and Written Opinion, PCT/US2013/033566, Oct. 15, 2013, 15 pages.

(Continued)

*Primary Examiner* — Max Noori
(74) *Attorney, Agent, or Firm* — John W. Wustenberg; Fish & Richardson P.C.

(57) ABSTRACT

Systems and methods provide for testing a cement by measuring both axial shrinkage/expansion and radial shrinkage/expansion of a sample.

21 Claims, 11 Drawing Sheets

(56) References Cited

U.S. PATENT DOCUMENTS

| | | | |
|---|---|---|---|
| 4,823,594 A | 4/1989 | Gray | |
| 4,848,145 A | 7/1989 | Blaschke et al. | |
| 4,893,285 A | 1/1990 | Masson et al. | |
| 4,896,303 A | 1/1990 | Leslie et al. | |
| 4,970,695 A | 11/1990 | Huau | |
| 5,009,512 A | 4/1991 | Lessi et al. | |
| 5,036,709 A | 8/1991 | McRae | |
| 5,089,989 A | 2/1992 | Schmidt et al. | |
| 5,127,473 A | 7/1992 | Harris et al. | |
| 5,159,828 A | 11/1992 | Steiger | |
| 5,216,638 A | 6/1993 | Wright | |
| 5,226,310 A * | 7/1993 | Steiger | 73/38 |
| 5,233,863 A | 8/1993 | Surjaatmadja et al. | |
| 5,248,200 A | 9/1993 | Walsh | |
| 5,325,723 A | 7/1994 | Meadows et al. | |
| 5,346,012 A | 9/1994 | Heathman et al. | |
| 5,353,637 A | 10/1994 | Plumb et al. | |
| 5,368,103 A | 11/1994 | Heathman et al. | |
| 5,377,160 A | 12/1994 | Tello et al. | |
| 5,377,753 A | 1/1995 | Haberman et al. | |
| 5,389,706 A | 2/1995 | Heathman et al. | |
| 5,412,990 A | 5/1995 | D'Angelo et al. | |
| 5,487,307 A | 1/1996 | Landgren et al. | |
| 5,488,994 A | 2/1996 | Laurel et al. | |
| 5,544,704 A | 8/1996 | Laurel et al. | |
| 5,571,951 A | 11/1996 | Jamth | |
| 5,572,021 A | 11/1996 | Heathman et al. | |
| 5,696,059 A | 12/1997 | Onan et al. | |
| 5,712,431 A | 1/1998 | Vilendrer | |
| 5,718,292 A | 2/1998 | Heathman et al. | |
| 5,741,971 A | 4/1998 | Lacy | |
| 5,763,773 A | 6/1998 | Birchak et al. | |
| 5,783,822 A | 7/1998 | Buchanan et al. | |
| 5,787,983 A | 8/1998 | Heathman et al. | |
| 5,836,200 A | 11/1998 | Belonenko et al. | |
| 5,869,750 A | 2/1999 | Onan et al. | |
| 5,964,293 A | 10/1999 | Chatterji et al. | |
| 5,968,255 A | 10/1999 | Mehta et al. | |
| 5,969,059 A | 10/1999 | Murai et al. | |
| 5,972,103 A | 10/1999 | Mehta et al. | |
| 5,992,223 A | 11/1999 | Sabrins et al. | |
| 5,996,693 A | 12/1999 | Heathman | |
| 6,019,835 A | 2/2000 | Chatterji et al. | |
| 6,053,245 A | 4/2000 | Haberman | |
| 6,055,874 A | 5/2000 | Onan et al. | |
| 6,060,434 A | 5/2000 | Sweatman et al. | |
| 6,070,662 A | 6/2000 | Ciglenec et al. | |
| 6,112,599 A | 9/2000 | Maki, Jr. | |
| 6,124,246 A | 9/2000 | Heathman et al. | |
| 6,134,954 A * | 10/2000 | Suresh et al. | 73/81 |
| H1932 H | 1/2001 | Heathman et al. | |
| 6,170,575 B1 | 1/2001 | Reddy et al. | |
| 6,209,646 B1 | 4/2001 | Reddy et al. | |
| 6,227,039 B1 | 5/2001 | Te'eni | |
| 6,227,294 B1 | 5/2001 | Chatterji et al. | |
| 6,245,142 B1 | 6/2001 | Reddy et al. | |
| 6,258,757 B1 | 7/2001 | Sweatman et al. | |
| 6,269,684 B1 | 8/2001 | Maki, Jr. et al. | |
| 6,270,565 B1 | 8/2001 | Heathman | |
| 6,345,535 B1 | 2/2002 | Sabins et al. | |
| 6,367,549 B1 | 4/2002 | Chatterji et al. | |
| 6,367,550 B1 | 4/2002 | Chatterji et al. | |
| 6,379,456 B1 | 4/2002 | Heathman et al. | |
| 6,444,316 B1 | 9/2002 | Reddy et al. | |
| 6,454,001 B1 | 9/2002 | Thompson et al. | |
| 6,478,868 B1 | 11/2002 | Reddy et al. | |
| 6,478,869 B2 | 11/2002 | Reddy et al. | |
| 6,484,568 B1 | 11/2002 | Griffith et al. | |
| 6,494,951 B1 | 12/2002 | Reddy et al. | |
| 6,510,743 B2 | 1/2003 | McAfee et al. | |
| 6,527,051 B1 | 3/2003 | Reddy et al. | |
| 6,527,438 B2 | 3/2003 | Zollinger et al. | |
| 6,547,871 B2 | 4/2003 | Chatterji et al. | |
| 6,554,071 B1 | 4/2003 | Reddy et al. | |
| 6,591,910 B1 | 7/2003 | Chatterji et al. | |
| 6,595,068 B2 | 7/2003 | Brovold et al. | |
| 6,610,139 B2 | 8/2003 | Reddy et al. | |
| 6,644,402 B1 | 11/2003 | Sharma et al. | |
| 6,655,213 B1 | 12/2003 | Reinhardt et al. | |
| 6,660,080 B2 | 12/2003 | Reddy et al. | |
| 6,711,941 B2 * | 3/2004 | Braithwaite et al. | 73/54.01 |
| 6,762,156 B2 | 7/2004 | Heathman et al. | |
| 6,767,867 B2 | 7/2004 | Chatterji et al. | |
| 6,782,735 B2 | 8/2004 | Walters et al. | |
| 6,789,621 B2 | 9/2004 | Wetzel et al. | |
| 6,797,054 B2 | 9/2004 | Chatterji et al. | |
| 6,817,238 B2 | 11/2004 | Go Boncan et al. | |
| 6,818,596 B1 | 11/2004 | Hayes | |
| 6,828,922 B1 | 12/2004 | Gremmert et al. | |
| 6,829,922 B2 | 12/2004 | Patin et al. | |
| 6,834,233 B2 | 12/2004 | Economides et al. | |
| 6,843,846 B2 | 1/2005 | Chatterji et al. | |
| 6,874,353 B2 | 4/2005 | Johnson et al. | |
| 6,892,814 B2 | 5/2005 | Heathman et al. | |
| 6,910,535 B2 | 6/2005 | Tare et al. | |
| 6,918,292 B2 | 7/2005 | Go Boncan et al. | |
| 6,951,249 B1 | 10/2005 | Chatterji et al. | |
| 6,964,302 B2 | 11/2005 | Luke et al. | |
| 6,978,835 B1 | 12/2005 | Reddy et al. | |
| 6,994,164 B2 | 2/2006 | Tare et al. | |
| 7,004,256 B1 | 2/2006 | Chatterji et al. | |
| 7,008,477 B2 | 3/2006 | Chatterji et al. | |
| 7,013,975 B2 | 3/2006 | Chatterji et al. | |
| 7,048,054 B2 | 5/2006 | Heathman et al. | |
| 7,089,816 B2 | 8/2006 | Hakimuddin | |
| 7,096,944 B2 | 8/2006 | Vargo, Jr. et al. | |
| 7,128,142 B2 | 10/2006 | Heathman et al. | |
| 7,128,149 B2 | 10/2006 | Heathman et al. | |
| 7,143,827 B2 | 12/2006 | Chatterji et al. | |
| 7,178,590 B2 | 2/2007 | Vargo, Jr. et al. | |
| 7,191,663 B2 | 3/2007 | Go Boncan et al. | |
| 7,222,676 B2 | 5/2007 | Patel et al. | |
| 7,240,545 B1 | 7/2007 | Jennings | |
| 7,244,303 B2 | 7/2007 | Chatterji et al. | |
| 7,255,170 B2 | 8/2007 | Chatterji et al. | |
| 7,284,898 B2 | 10/2007 | Duell et al. | |
| 7,285,166 B2 | 10/2007 | Luke et al. | |
| 7,296,927 B2 | 11/2007 | Reddy et al. | |
| 7,325,629 B2 | 2/2008 | Blaschke et al. | |
| 7,373,982 B2 | 5/2008 | Brothers et al. | |
| 7,380,466 B2 * | 6/2008 | Deeg | 73/803 |
| 7,549,320 B2 | 6/2009 | Funkhouser et al. | |
| 7,552,648 B2 | 6/2009 | McMechan et al. | |
| 7,621,186 B2 | 11/2009 | Heathman et al. | |
| 2001/0001381 A1 | 5/2001 | Reddy et al. | |
| 2001/0037687 A1 | 11/2001 | Brovold et al. | |
| 2003/0140707 A1 | 7/2003 | Pyle et al. | |
| 2003/0150263 A1 | 8/2003 | Economides et al. | |
| 2003/0161211 A1 | 8/2003 | Duell et al. | |
| 2003/0221829 A1 | 12/2003 | Patel et al. | |
| 2004/0054262 A1 | 3/2004 | Horak | |
| 2004/0055392 A1 | 3/2004 | Patin et al. | |
| 2004/0154263 A1 | 8/2004 | Li et al. | |
| 2004/0221990 A1 | 11/2004 | Heathman et al. | |
| 2004/0226483 A1 | 11/2004 | Chatterji et al. | |
| 2005/0009710 A1 | 1/2005 | Heathman et al. | |
| 2005/0080161 A1 | 4/2005 | Tare et al. | |
| 2005/0109507 A1 | 5/2005 | Heathman et al. | |
| 2005/0126300 A1 | 6/2005 | Go Boncan et al. | |
| 2005/0135185 A1 | 6/2005 | Duell et al. | |
| 2005/0152432 A1 | 7/2005 | Hakimuddin | |
| 2005/0204960 A1 | 9/2005 | Heathman et al. | |
| 2006/0000612 A1 | 1/2006 | Reddy et al. | |
| 2006/0225523 A1 | 10/2006 | Reddy et al. | |
| 2006/0258545 A1 | 11/2006 | Chatterji et al. | |
| 2007/0012441 A1 | 1/2007 | Heathman et al. | |
| 2007/0056383 A1 | 3/2007 | Deeg | |
| 2007/0082822 A1 | 4/2007 | Kirsner et al. | |
| 2007/0105995 A1 | 5/2007 | Chatterji et al. | |
| 2007/0169937 A1 | 7/2007 | Allin et al. | |
| 2007/0173412 A1 | 7/2007 | Allin et al. | |
| 2008/0168848 A1 | 7/2008 | Funkhouser et al. | |
| 2008/0178683 A1 | 7/2008 | Heathman et al. | |
| 2008/0197605 A1 | 8/2008 | Blaschke et al. | |

(56) References Cited

U.S. PATENT DOCUMENTS

| | | | |
|---|---|---|---|
| 2009/0084189 | A1 | 4/2009 | McMechan et al. |
| 2011/0061525 | A1 | 3/2011 | Gray et al. |
| 2011/0094295 | A1 | 4/2011 | Meadows et al. |

FOREIGN PATENT DOCUMENTS

| | | | |
|---|---|---|---|
| EP | 0 176 400 B1 | 4/1986 | |
| EP | 0 101 580 B1 | 12/1986 | |
| EP | 0 110 750 B1 | 9/1988 | |
| EP | 0 098 778 B1 | 3/1989 | |
| EP | 0 198 985 B1 | 12/1989 | |
| EP | 0 443 936 A1 | 8/1991 | |
| EP | 0 395 499 B1 | 7/1993 | |
| EP | 0 176 408 B1 | 4/1996 | |
| EP | 1 189 051 | 2/2001 | |
| EP | 0 865 612 B1 | 6/2002 | |
| EP | 1 541 987 | 6/2005 | |
| FR | 2 340 551 | 9/1977 | |
| FR | 2 746 920 | 10/1997 | |
| FR | 2 965 925 | 4/2012 | |
| GB | 2 353 546 A | 2/2001 | |
| GB | 2 354 026 A | 3/2001 | |
| GB | 2 355 742 A | 5/2001 | |
| GB | 2 386 625 A | 9/2003 | |
| WO | WO 00/49273 | 8/2000 | |
| WO | WO 2004/008302 A1 | 10/2004 | |
| WO | WO 2005/065411 | 7/2005 | |
| WO | WO2008/084201 | 7/2008 | |
| WO | WO2010/094925 | 8/2010 | |

OTHER PUBLICATIONS

Deeg, Wolfgang, et al., "*How Foamed Cement Advantages Extend to Hydraulic Fracturing Operations*," World Oil, Nov. 1999, pp. 51-53.

Dillenbeck, R.L., GoBoncan, V., and Rogers, M.J., "*Testing Cement Static Tensile Behavior Under Downhole Conditions*," SPE 97967, Society of Petroleum Engineers, Copyright 2005, 12 pages.

FlexiForce®, materials downloaded from Tekscan website (www.tekscan.com) on FlexiForce® sensors), http://www.tekscan.com/flexiforce.html, visited Aug. 3, 2005, 20 pages.

Goodwin, K.J., "*Cement Sheath Stress Failure*," SPE Drilling Engineering, SPE 20453, Dec. 1992, pp. 291-296, and additional pp. 501-508 from SPE 20453.

Love, A.E.H., "*A Treatise on the Mathematical Theory of Elasticity*," Fourth Edition, Dover Publications, New York, 1944, pp. 144-145.

Minear, John W. and Goodwin, K. Joe, "*Cement-Sheath Evaluation*," Chapter 10, Petroleum Well Construction, John Wiley & Sons Publisher, ISBN 0-471-96938-9, copyright 1998, front and back cover and pp. 271-296.

Thiercelin, J.J., et al., "Cement Design Based on Cement Mechanical Response," *SPE Drilling & Completion*, Society of Petroleum Engineers, SPE 52890, Dec. 1998, pp. 266-273.

"Standard Test Method for Tensile Strength of Hydraulic Cement Mortars", ASTM Standards, C-190-85, pp. 197-202, Year 1990.

Bridgman, P.W., "V. Breaking Tests Under Hydrostatic Pressure and Conditions of Rupture", *Philosophical Magazine and Journal of Science*, vol. 24, Sixth Series, pp. 63-80, (1912).

Clayton, N. et al., "The Diphase Concept, With Particular Reference to Concrete", *Developments in Concrete Technology*, vol. 1, F. D. Lydon, Ed.; Applied Science Publisher Ltd, Chapter 7, pp. 283-318, (1979).

Clayton, N., "Fluid-pressure Testing of Concrete Cylinders," *Magazine of Concrete Research*, vol. 30, No. 102, pp. 26-30, (1978).

Mindess, S. et al., "The Nitrogen Gas Tension Test of Concrete", Proceedings of ConMat '05 and Mindess Symposium, Aug. 22-24, 2005, The University of British Columbia, Vancouver, Canada, 8 pages, (2005).

Richart, Frank E. et al., "A Study of the Failure of Concrete Under Combined Compressive Stresses", The University of Illinois—Engineering Experiment Station, Bulletin No. 185, pp. 3-253, (1928).

Sabins, Fred, "MMS Project Long-Term Integrity of Deepwater Cement Systems Under Stress/Compaction Conditions", CSI Technologies, Sep. 3, 2004.

Gary Funkhouser et al., "Measuring Cement Properties" U.S. Appl. No. 11/622,255, filed Jan. 11, 2007 (25 pages).

Wolfgang F. J. Deeg, "Apparatus and Method for Determining Mechanical Properties of Cement for a Well Bore" U.S. Appl. No. 11/206,719, filed Aug. 18, 2005 (32 pages).

David Leon Meadows et al., "Cement Testing" U.S. Appl. No. 12/607,560, filed Oct. 28, 2009 (33 pages).

David Leon Meadows et al., "Cement Testing" U.S. Appl. No. 13/409,745, filed Mar. 1, 2012 (43 pages).

Invitation to Pay Additional Fees and Partial Search Report in International Application No. PCT/US2013/033566, mailed Jul. 18, 2013, 5 pages.

\* cited by examiner

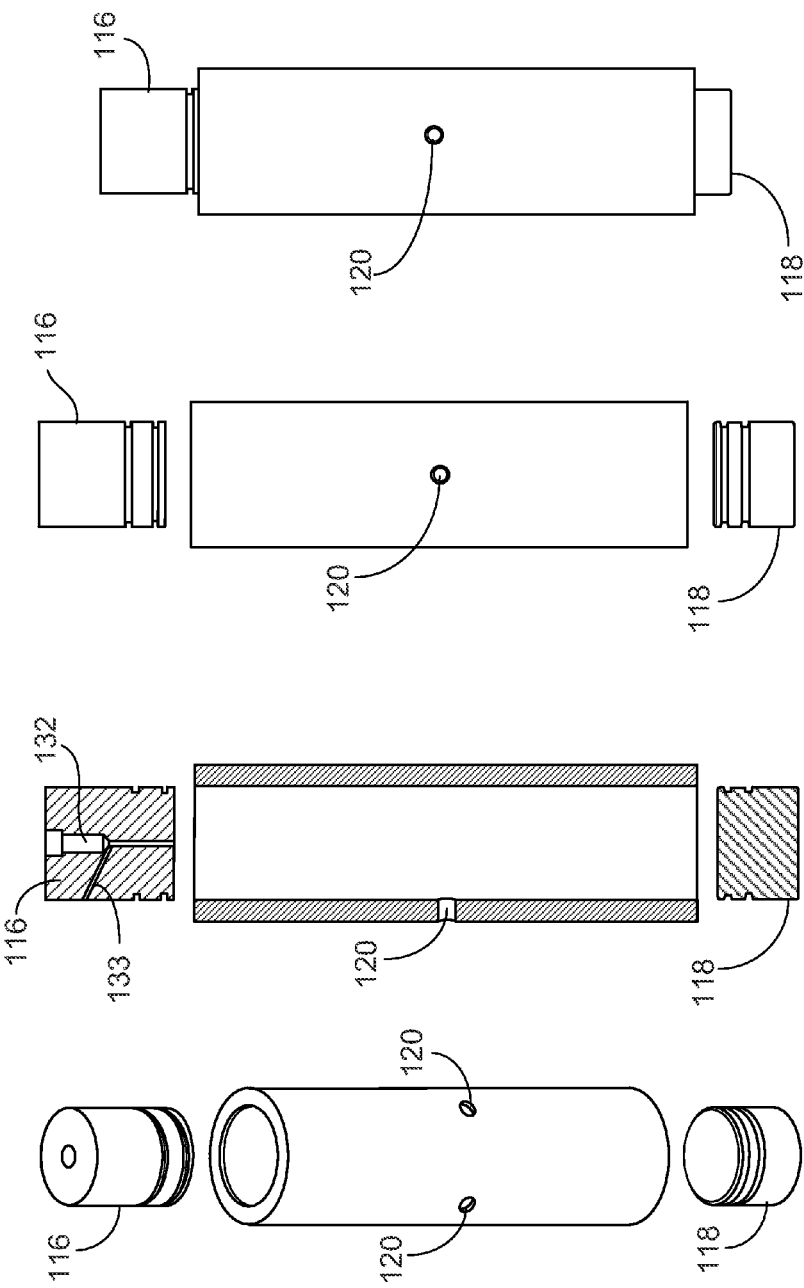

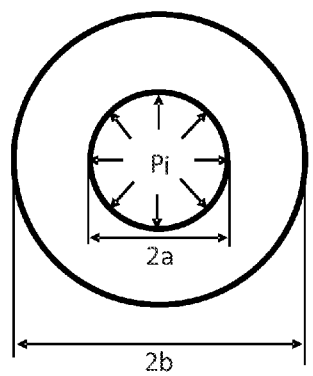
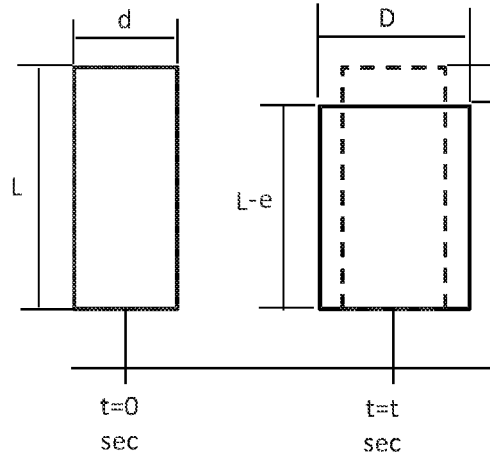
FIG. 2A                FIG. 2B
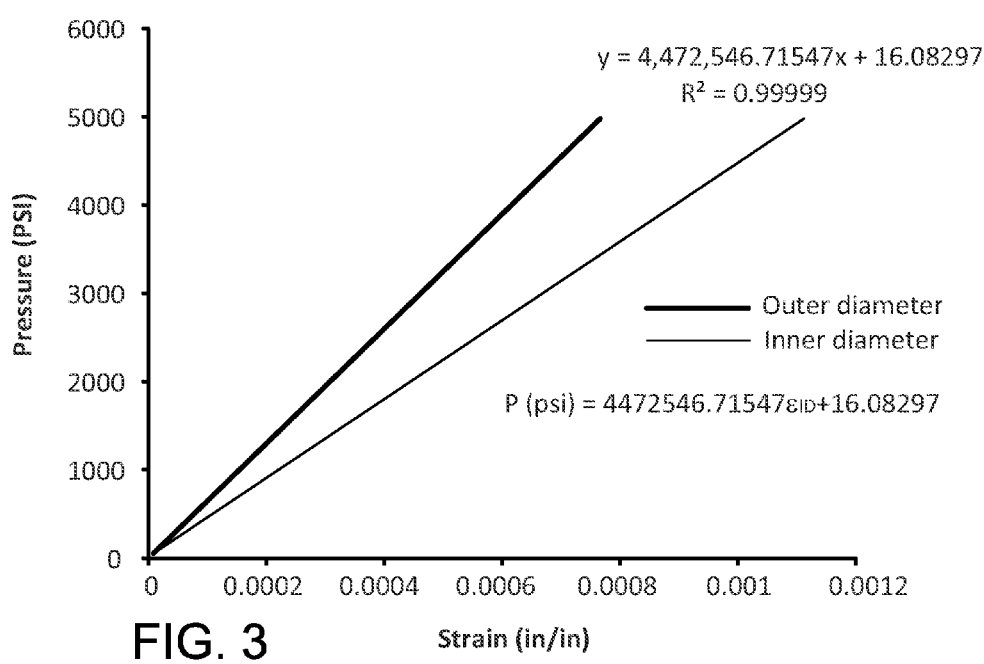
FIG. 3

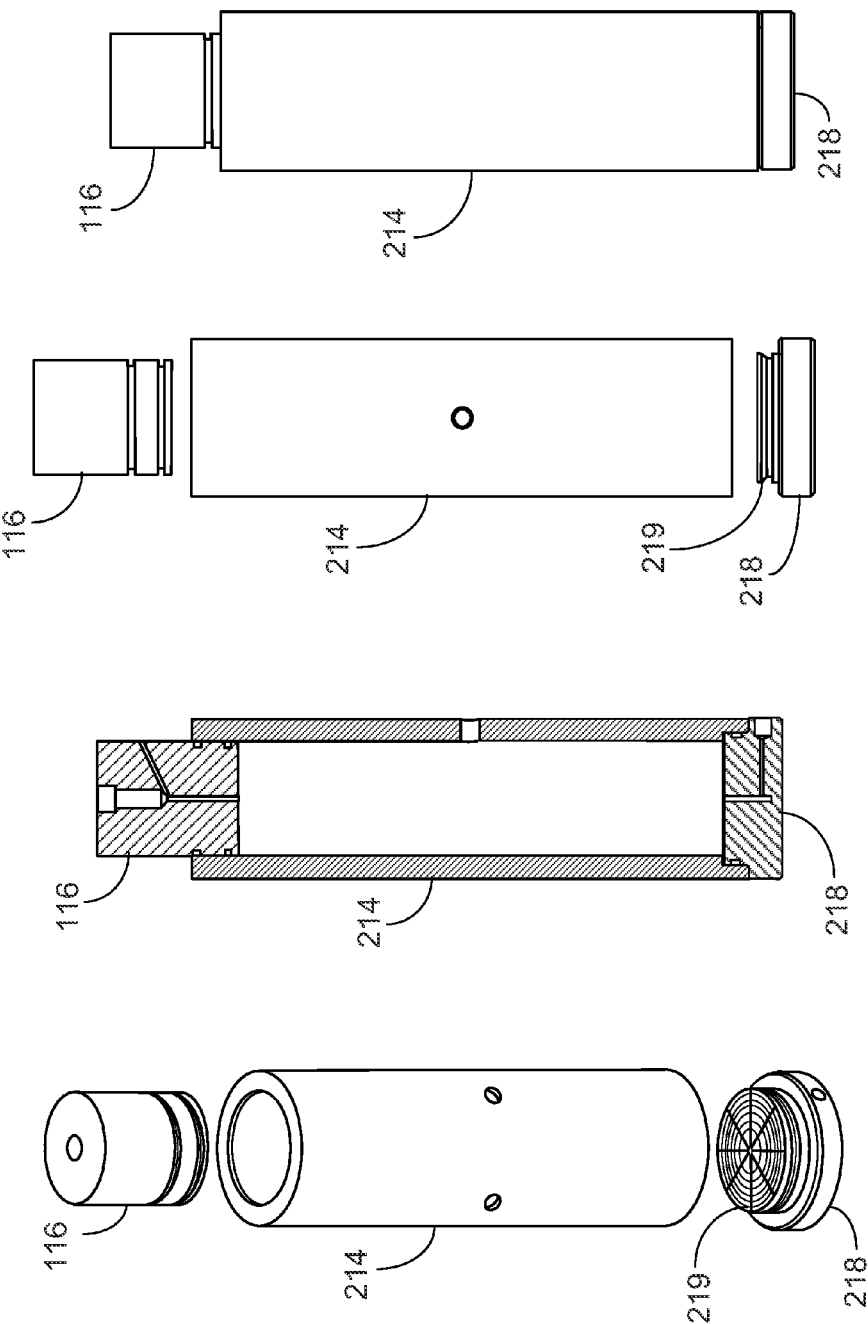

CEMENT TESTING

TECHNICAL FIELD

This disclosure relates to measuring mechanical properties.

BACKGROUND

Some well bores, for example some oil and gas wells, are lined with a casing. The cemented casing stabilizes the sides of the well bore, prevents fluids (liquids or gases) in the well bore from entering the surrounding earth formations, and/or prevents fluids from zones other than the producing zones from entering the well bore.

In a typical cementing operation, cement is introduced down the well bore and into an annular space between the casing and the surrounding earth. The cement secures the casing in the well bore, and prevents fluids from flowing vertically in the annulus between the casing and the surrounding earth.

Different cement formulations are designed for a variety of well bore conditions, which may be above or below ambient temperature and/or above ambient pressure. In designing a cement formulation, a number of potential mixtures may be evaluated to determine their mechanical properties under various conditions.

SUMMARY

Using the devices and methods described, the volumetric shrinkage/expansion resulting from cement hydration can be directly and continuously correlated to the Initial Stress State of curing-cement under simulated wellbore conditions of pressure and temperature. This parameter will define the initial distance the material is from failure or the stress state of the material prior to additional loading. This turns out to be a key parameter when employing long term cement-sheath modeling based on the initial state of stress added to the stress variations that the material will be subjected to owing to the long term requirements dictated by well operations during the economic life of the well.

Even though mechanical properties of cement are, up to some extent, known before material placement in the well, it is important to note that there is no advantage to knowing the total capacity of a material without prior determination of its initial stress of state as the erroneous determination of this parameter can lead to incorrect conceptions on whether or not a material will withstand a specific set of loadings. The test cell is designed in such a way that both radial and axial shrinkage/expansion are continuously monitored while cement hydrates.

In one aspect, methods for testing a sample of a fluid mixture that hardens into a solid include: placing the sample of the fluid mixture into a test chamber; applying a pressure to the sample in the test chamber that is different than ambient air pressure around the test chamber; taking the samples in the test chamber to the desire temperature setting; monitor axial dimensions and radial dimensions of the sample over time; and identifying an initiation of gelling and hardening of the sample by a start of changes to the radial dimensions of the sample.

In one aspect, methods for testing a sample of a fluid mixture that hardens into a solid include: placing the sample of the fluid mixture into a test chamber; and identifying a stress state of a sample of the cement at/after an initiation of gelling and hardening of the sample.

In one aspect, methods for assessing a cement include: identifying a stress state of a sample of the cement at an initiation of gelling and hardening of the sample; using the identified stress state of the sample of the cement as an initial stress state parameter input into a computer well model; and performing well life modeling of the of the cement using the computer well model.

Embodiments of these methods can include one or more of the following features.

In some embodiments, methods also include determining an initial stress state of the sample by calculating a stress state of the sample at the identified initiation of gelling of the sample.

In some embodiments, methods also include controlling a temperature of the test chamber.

In some embodiments, the test chamber comprises an annular portion.

In some embodiments, methods also include developing a calibrated stress-strain relationship for the test chamber by pressurizing the test chamber in the absence of a sample and recording pressure and strain.

In some embodiments, methods also include applying conditions in the test chamber after the sample cures to simulate well operation events.

In some embodiments, methods also include applying a first pressure to bottom surfaces of the sample and a different second pressure to top surfaces of the sample.

In some embodiments, methods also include measuring strain at multiple locations distributed axially along the test chamber. In some cases, methods also include assessing heterogeneity of gelling and hardening of the sample based on differences in the strain measured at the multiple locations distributed axially along the test chamber.

In some embodiments, methods also include performing shear and/or hydraulic bond testing on the sample in the test chamber.

In some embodiments, methods also include identifying the initiation of gelling and hardening of the sample by a start of changes to the radial dimensions of the sample.

In some embodiments, methods also include applying a pressure to the sample in the test chamber that is different than ambient air pressure around the test chamber.

In some embodiments, methods also include monitoring axial dimensions and radial dimensions of the sample over time.

In some embodiments, methods also include applying conditions in the test chamber after the sample cures to simulate well operation events.

In some embodiments, performing well life modeling comprises simulating at least one of cementing, pressure testing, swabbing, hydraulic fracturing, and production.

In some embodiments, methods also include simulating application of stresses to a virtual cement sheath in the computer well model estimate a distance to failure for the cement under different conditions.

The described methods and systems can provide one or more of the following advantages.

Both chemical shrinkage and bulk shrinkage of cements are influenced by temperature and pressure conditions. These methods and systems can be used to determine stress changes experienced by cement due to hydration shrinkage/expansion while cement cures under the downhole conditions (e.g., below or above atmospheric temperatures and above atmospheric pressures). In particular, these methods and systems can provide a calculation of the initial stress state a cement sheath will experience in specific downhole applications.

This parameter is critical when modeling long term events that occur during the life of a well.

This technique measures a stress change that a cement will experience and can directly address the concerns about determining the initial stress state of cement. The initial stress state of set cement calculated using these methods and systems is anticipated to be more accurate than prior methods that investigate chemical shrinkage or bulk shrinkage but not both. In particular, these methods and systems avoid the complicated and controversial analysis necessary to derive an initial stress state of the set cement that can be used for stress analysis from other approaches.

The development of analytical models to simulate material behavior under certain conditions applies knowledge of various parameters such as geometry, failure criteria, loading history, constitutive law (relation between physical parameters that allow for material characterization), and the initial stress of state. Besides determining the initial state of stress of hydrating cement, the device and method described herein can also be employed to determine various physical parameters that comprise constitutive law that emulate the behavior of cement. Other parameters employed to characterize cement behavior such as shear and hydraulic bond under different wellbore conditions can also be correlated to the shrinkage/expansion measurements.

The method apparatus described herein also has the potential to measure hydrostatic pressure loss experienced by the cement during hydration, which is directly related to static gel strength; as well as widely considered a reason for early gas migration.

The details of one or more embodiments are set forth in the accompanying drawings and the description below.

DESCRIPTION OF DRAWINGS

FIGS. 1B-1E are, respectively, an exploded perspective view, a exploded cross-sectional view, an exploded side view, and an assembled side view of the testing apparatus of FIG. 1A.

FIG. 2 is a schematic illustrating axial compression and radial expansion of a sample.

FIG. 3 shows a plot of the relationship between strain and pressure used in calibration of a testing apparatus. This will allow for correlation of hydrating shrinkage/expansion to the state of stress of cement.

FIGS. 12B-12E are, respectively, an exploded perspective view, an exploded cross-sectional view, an exploded side view, and an assembled side view of the testing apparatus of FIG. 12A.

Like reference symbols in the various drawings indicate like elements.

DETAILED DESCRIPTION

Cements can be used, for example, to seal an annular space in wellbore between a well casing and the surrounding formation. Understanding the shrinkage/expansion properties of cements under different conditions can be important in designing/choosing an appropriate cement for a specific application. The described devices and methods incorporate a test chamber capable of directly and continuously measuring sample shrinkage/expansion at different pressure and temperature conditions. Both axial shrinkage/expansion and radial shrinkage/expansion of the sample are continuously measured and correlated to the initial stress state of cement sheath under simulated wellbore conditions.

As used herein, "cement" and "cement composition" encompass a fluid mixture that hardens into a solid, and may be any agent suitable to bond casing or other elements (e.g. tubulars) to well bore walls or to other tubing used for downhole applications. Some examples of cement include hydraulic cement (e.g., Portland cement formulations), non-hydraulic cement (e.g., polymer resin formulations), and mixtures thereof having, for instance, silica, Pozzolans, cross-linked polymers, ceramics, among other components. As used herein, "curing" refers to the reactions through which cement hardens from a fluid mixture into a solid. In some instances, the devices and methods discussed herein can be used to measure mechanical properties at temperatures and pressures that simulate downhole conditions.

Figure 1A:
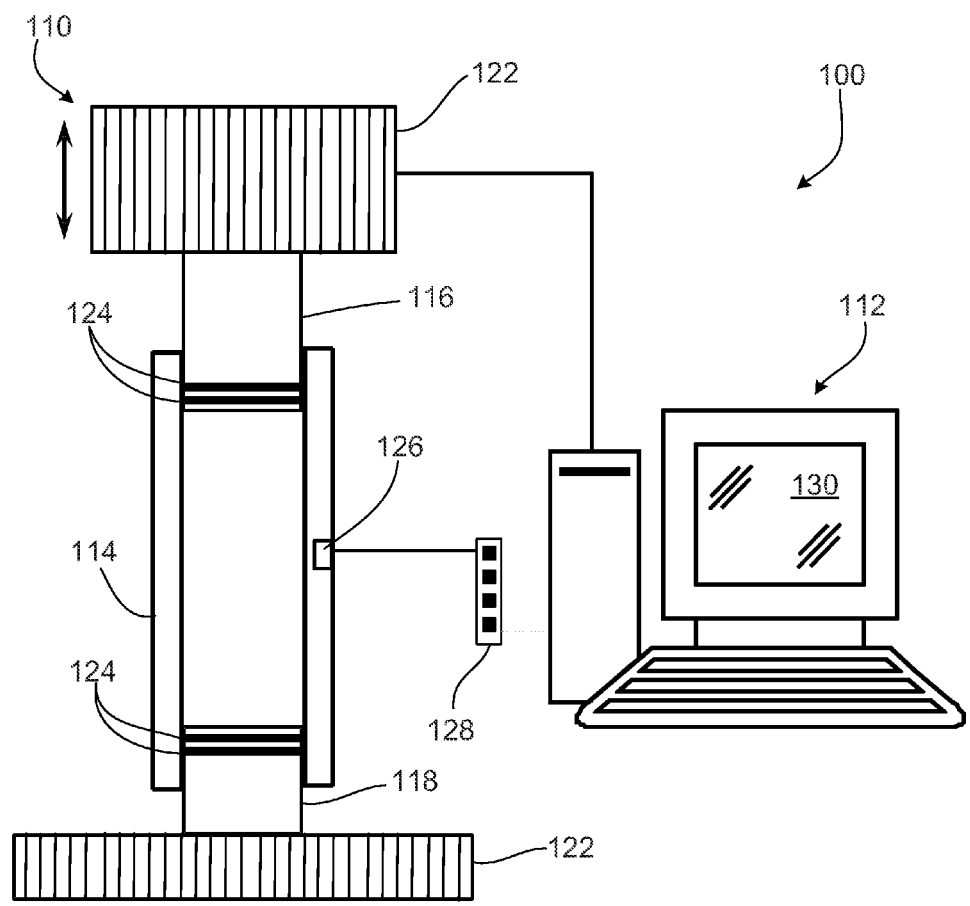
FIG. 1A is a schematic of a testing apparatus.

FIG. 1A illustrates a testing system 100 that includes a test cell 110 and a data acquisition system 112. FIGS. 1B-1E further illustrate features of the test cell 110 which includes a test chamber 114, a top piston 116, and a bottom piston 118. In this description, terms of relative orientation such as upper, lower, above, and below are used relative to the orientation of embodiments shown in the figures being discussed. Although such terms do not require that the illustrated devices be oriented as shown in the figures, the test cell 110 will typically be oriented as shown in FIG. 1A during use.

As used herein, "piston" encompasses driving mechanisms including, for example, hydraulic pistons, power screws, and linear actuators. Thus, the piston does not necessarily seal against the pressure vessels described below.

In testing system 100, the test chamber 114 is a hollow metallic cylinder. The test chamber 114 is formed of material which is structurally stable enough to contain a sample at pressures and temperatures simulating downhole conditions (e.g., up to 10,000 psi and 600 F) are applied to the sample and which measurably deforms as the sample shrinks/expands during curing. In one prototype, the test chamber 114 was machined from brass and, in another prototype, the test chamber 114 was machined from bronze alloy. Alternatively, the test chamber 114 can be formed using casting, laminating, or molding techniques from materials including, for example, steel, alloys, or composite fibers with a resin structure. Ports 120 (see FIGS. 1B-1E) extend through walls of the test chamber and provide access for sensors (not shown) used to measure sample conditions. For example, test chamber 114 defines a first port for a thermocouple used to measure sample temperature and a second port for a pressure sensor.

The top piston 116 is operable to apply a load to a sample in the test cell 114. Testing system 100 includes a load frame 122 operable to generate loads transmitted to the sample in the test cell 114. A prototype testing system was implemented with an Instron series 5884 load frame. Some testing systems include other mechanisms (e.g., power screws, linear actuators, and pressure pumps) can be used to generate loads transmitted to the sample in the test cell 114. The top piston 116 defines a port 132 extending through the top piston. A side bleeding channel 133 extends at an angle from the port 132. A screw (not shown) is employed to block the bleeding channel 133 once the cell 114 is filled with the slurry and all the air is removed.

The bottom piston 118 is fixed in place relative to the test chamber 114 acting only as a bottom cap. However, some test cells include bottom pistons that are moveable relative to the test chamber 114.

During use, the temperature of fluid in the test can range from below ambient condition temperatures to the high temperatures associated with downhole conditions (e.g., up to 1000 degrees Fahrenheit). The pressure of the fluid in the pressure vessel can range from atmospheric pressure to the high pressures associated with downhole conditions (e.g., up to 60,000 psi). The components of the pressure vessel can be made from materials which are strong (e.g., able to maintain structural stability when subjected to high pressures), are durable (e.g., resistant to corrosion by the anticipated pressurizing fluids in the anticipated temperature and pressure ranges), and can be formed with the precision necessary to maintain substantially pressure-tight engagement between the components under testing conditions. For example, the test chamber 114, the top piston 116, and the bottom piston 118 can be machined from stainless steel. Alternatively, the test chamber 114, the top piston 116, and the bottom piston 118 can be formed using casting, laminating, or molding techniques from materials including, for example, steel, alloys, or composite fibers with a resin structure.

Seals between inner walls of the test cell 114 and outer surfaces of the pistons 116, 118 limit (e.g., substantially prevent or prevent) fluid flow out of the test cell 114 between the inner walls of the test chamber 114 and outer surfaces of the pistons 116, 118. Test cell 110 includes O-ring seals 124 attached to both the bottom and top pistons in order to avoid fluid losses. In some embodiments, testing systems use other sealing mechanisms including, for example, matching threads, gaskets, or metal-to-metal seals.

Some testing systems 100 include temperature-control mechanisms to simulate downhole temperatures during testing. External or internal heating elements may be employed to keep the desired temperature on the cement slurry; or the testing apparatus could be placed in an oven for heating purposes. Examples of external heating elements include heating coils or stainless steel heating bands and, internal heating coils include, for example, internal electrical resistances inside the hydraulic fluid. There are applications where the temperature below ambient conditions are present in the wellbore. Cooling coils can be employed to take the cement specimen to the desire conditions and allow for its controlled curing. A double purpose heating/cooling system may be employed, where a hot fluid is employed when temperatures higher that ambient conditions are required; or a refrigerant is employed when temperature below ambient conditions are required.

In some embodiments, pressure and temperature controllers are used in such way that (a), downhole conditions are simulated during cement transferring, curing and testing; and (b) these conditions are accurately maintained or shift according to the downhole conditions. For instance, cement slurry and testing apparatus can be preheated during mixing. The testing apparatus can be heated in a sequence that simulates the temperature conditions that a cement system would encountered from mixing, placement, and curing during the cementing a wellbore casing string. In addition, the test apparatus can simulate other well operation events that the cement system may be exposed to including, for example, pressure testing, steam injection, fracturing, and hydrocarbon production. As anticipated, tests performed using a prototype testing apparatus have confirmed that changes in the curing temperature and pressure change the properties or mechanical response of the cement sample.

Testing systems can include sensors to measure parameters used to calculate properties of samples being tested. For example, testing system 100 includes sensors to measure the axial and radial deformation of samples being tested. The sensors are in communication with the data acquisition system 112. In testing system 100, a strain gauge 126 monitors the radial deformation of the sample due to the cement slurry volume change. Sensors associated with the mechanism applying a load to the top piston 116 (e.g., load frame 122) monitor axial deformation of the sample and applied load. Some testing systems include other monitoring mechanism including, for example, linear variable displacement transducers (LVDTs), extensometers, lasers, DVRTs, or fiber optic strain gauges, can be used in addition to or in place of the strain gauges to measure relevant parameters. Pressure and temperature sensors can be included to measure pressures and temperatures present during testing. Pressure, temperature, and strain sensors can be used as feedback to control the test process. For example, pressure sensors can control the pump to pressure up or down dependent upon a controlled set point. Likewise, the piston loading the test specimen can be actuated in a direction depending on the deflection or strain measurements experienced by the sample.

In the prototype, a 120 ohms strain gauge connected with a high speed NI-USB-9192 data acquisition card 128 monitored radial deformation of the sample due to the cement slurry volume change. Bluehill® software for Instron load frame continuously recorded the axial displacement of samples and the applied load on the top piston during testing. The strain gauge and the Instron load frame communicated data to a desktop computer 130 with Bluehill® and LabVIEW software installed.

For a test chamber 114 that is a thick walled cylinder, the relationship between hoop strain of the outer surface and the strain in the inner surface is given by the Lame's solution for thick-wall cylinder as $$\frac{\varepsilon_{\theta,a}}{\varepsilon_{\theta,b}} = \frac{[(a^2+b^2) - v(a^2-b^2)]}{2a^2}$$

where $\epsilon_{\theta,a}$ is strain in the inner surface of the test chamber 114, $\epsilon_{\theta,b}$ is strain in the outer surface of the test chamber 114, a is the inner radius of the test chamber 114 (see FIG. 2A), b is the outer radius of the test chamber 114 (see FIG. 2A), and v is the Poisson ratio for the material used to form the test chamber 114. Given the known dimensions of the test chamber a, b and the Poisson ratio, it is possible to calculate the strain in the inner surface of the test chamber 114 ($\epsilon_{\theta,a}$) based on the strain in the outer surface of the test chamber 114 ($\epsilon_{\theta,b}$) as measured using the strain gauge 126.

Before use, the test system 100 is calibrated to develop the correlation between pressure applied to a sample and strain in the inner surfaces of the test chamber 114. The test chamber 114 is filled with water and pressure is applied to the water using the load frame 122. The applied pressure and strain in the outer surfaces of the test chamber 114 are measured and strain in the inner surfaces of the test chamber 114 is calculated based on the measured strain in the outer surface of the test chamber 114 using the equation above. FIG. 3 presents the data obtained when the prototype test cell 110 was calibrated using this approach. For the prototype test cell 110, the regression analysis performed using an Excel spreadsheet indicated that $$P = 44,725,46.7\epsilon_{\theta,a} + 16.1$$

where P is pressure (psi) and represents the stress on the sample. This equation can be used to convert strain measured on outer surfaces of the test chamber 114 to the stress state of the sample due to hydrating shrinkage/expansion. The relationship, which is specific to each individual test cell 110, can be used to determine downhole stresses on a cement sample.

Prior to testing a sample, a user assembles the test chamber 114 and the bottom piston 118, the chamber is filled to a desired level with a slurry of cement being tested. Once the chamber is filled, the top piston 116 is placed in the test chamber 114 while port 133 is used as a bleeding port for air removal. This is followed by positioning a special design screw (not shown) in port 132 to seal the test cell 110. After the test cell 110 is placed in the loading device (e.g., load frame 122), the user operates the testing system 100 to bring the slurry to conditions that simulate downhole temperature and pressure. For example, the load frame 122 can be used to apply pressure to the slurry via the top piston 116. As shown in FIG. 2B, the sample changes shape both radially and axially during testing. The test system 100 records the displacement of top piston 116 and the radial dimensions of the vessel while controlling the pressure applied to the top piston 116. The relationship developed during the cell calibration of pressure versus strain can be used to determine the stress change in the cement during testing. It has been observed that shrinkage/expansion occurring while the cement is still a liquid only results in the movement of the piston because the cell is still under constant pressure. In contrast, shrinkage/expansion that occurs once the cement starts to gel and/or harden results in both movement of the piston 116 and radial changes in the cell dimensions. The radial change in the cell dimensions result due to cement hydration which is reflected in a change of the pressure the cement applies to the cell. This is directly related to the stress that the cement experiences. The stress measured by testing cell 100 can then be used as input in well modeling. These models essentially create a virtual wellbore and simulate several events that occur during the life of the well. For example, a virtual wellbore is constructed by the software and then progresses through the life of the well simulating events such as cementing, pressure testing, swabbing fluids out, hydraulic fracturing and production. Stresses are applied to the cement sheath and analysis estimates the cement's remaining capacity for failure. In order to determine this distance to failure due to the different events, the initial state of stress of the cement sheath is a key model input.

A prototype testing system 100 was implemented using a brass test chamber 114 that provided an adequate ratio of resistance and flexibility to generate anticipated radial deformations. The top 116 and bottom pistons 118 were made of stainless steel-316. The top piston 114 had bleeding port 133 for air removal and a port 132 for positioning of special design screw (not shown) for sealing the test cell 100.

The prototype testing system was used to test properties of cements under various conditions. Initial experiments were conducted on a 16.4 lb/gal slurry over 48 hours. The load frame 112 applied pressure at a load rate of 2,000 lb-f/min until a constant load of 25,450 lbf (4,962 psi) was achieved.

Figure 4:
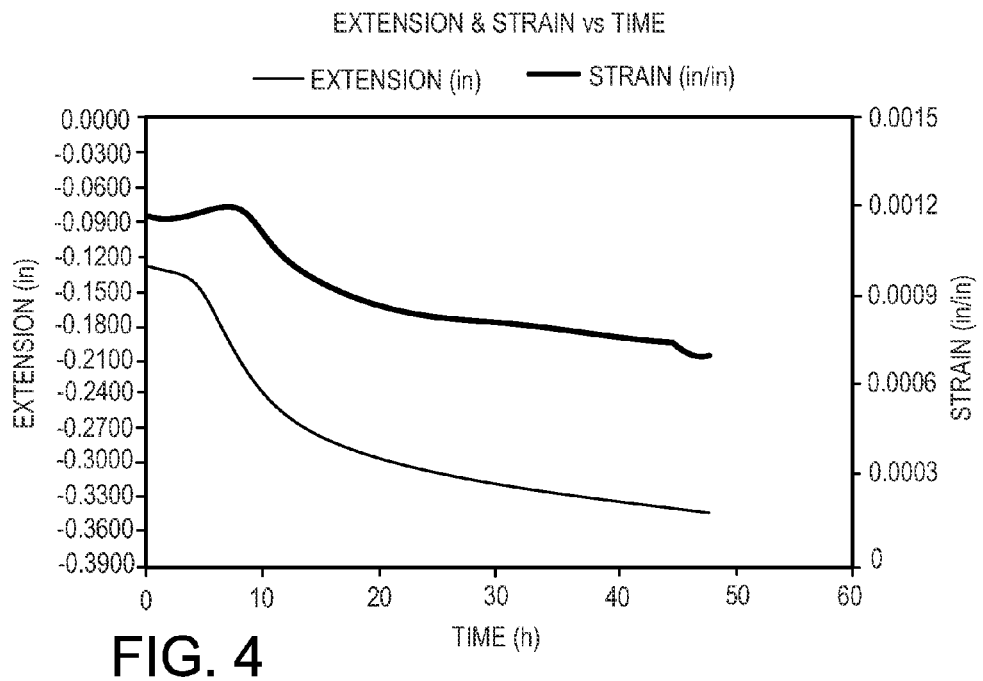
FIG. 4 shows axial extension and radial strain over 48 hours as a sample cures.

FIG. 4 shows the extension (axial displacement) and the strain (radial displacement) curves with respect to time. During the first 12 to 15 minutes of the test, the strain and axial displacement rapidly increased during the pressurization stage. The increase in strain during 3-8 hrs might have been a result of heat of hydration considering that the strain gages were not temperature compensated. From 8.5 to about 18 hours, there was a rapid decrease for both radial strain and axial displacement which is in agreement with the period where heat of hydration kicks in. The rate of change of radial strain and axial displacement slowed down after 18 hrs, however, these properties kept decreasing owing to hydration.

Figure 5:
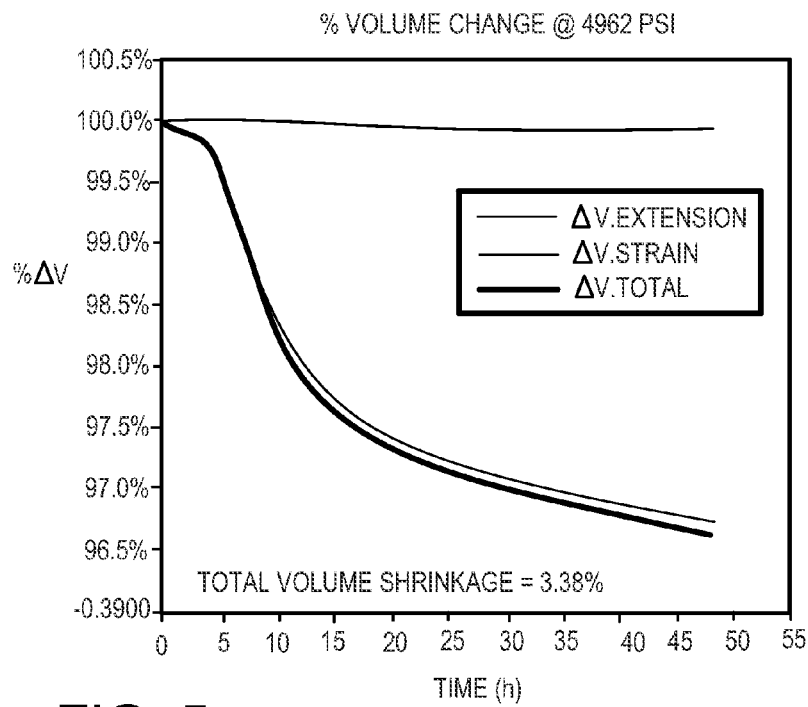
FIG. 5 shows volume change due to axial extension, volume change due to radial strain, and total volume change over 48 hours as a sample cures.
Figure 6:
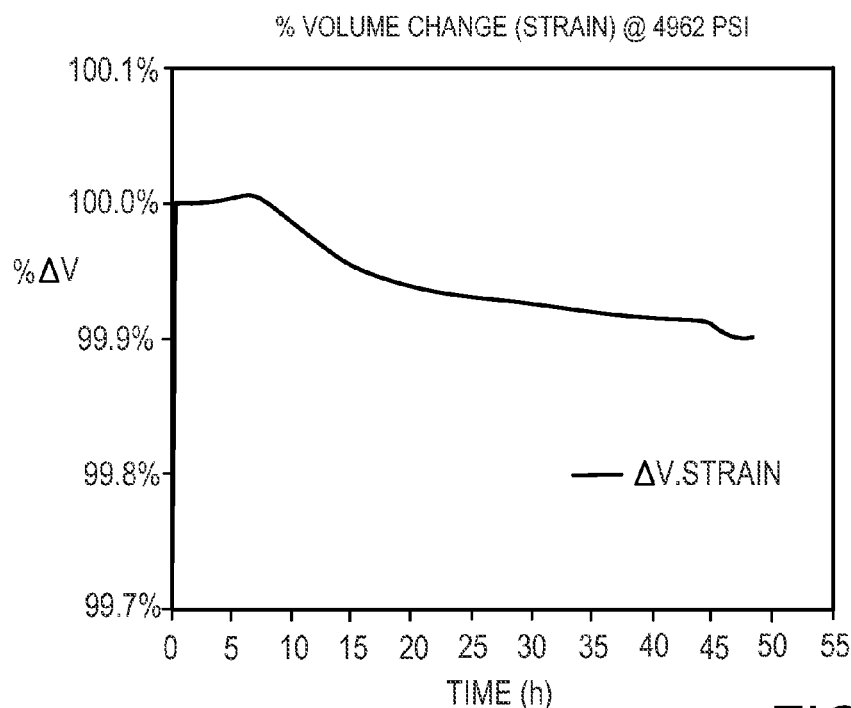
FIG. 6 shows volume change due to radial strain over 48 hours as a sample cures.
Figure 7:
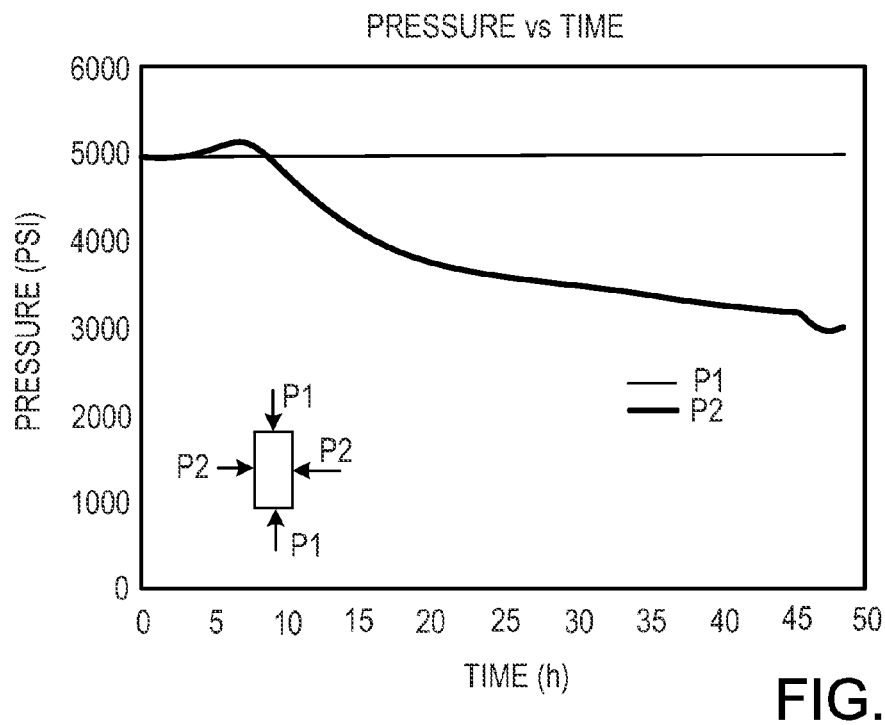
FIG. 7 shows axial pressure and radial pressure over 48 hours as a sample cures.

FIGS. 5 and 6 illustrate the total shrinkage volume and the shrinkage volume due to the axial and radial displacement. FIG. 7 shows the change in stress over time. A total shrinkage volume of 3.38% was observed after 48 hours. Most (97%) of the total shrinkage was due to the axial displacement, which corresponds to be 3.28%. Conversely, the radial displacement accounted for 0.1% of volume shrinkage, what would seem to be an insignificant amount of the total volume shrinkage. It is important to note that the radial shrinkage, a minute percentage of the total volumetric shrinkage, resulted in a pressure drop equivalent to ~2000 psi (see, e.g., FIG. 7).

The prototype testing system 100 demonstrated the capability to measure stress changes experienced by the cement due to hydration shrinkage/expansion. In addition to providing accurate volume shrinkage results, this method of testing also provides the capability of identifying the precise time at which shrinkage measurement should commence considering its effect on the stress state of cement.

Figure 8:
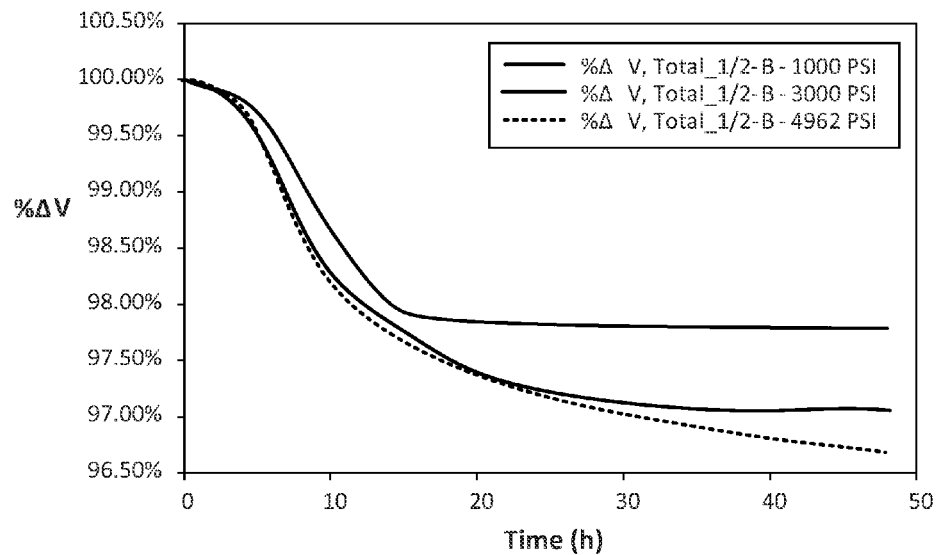
FIG. 8 compares the change in volume of samples as a function of time for different curing pressures.
Figure 9A:
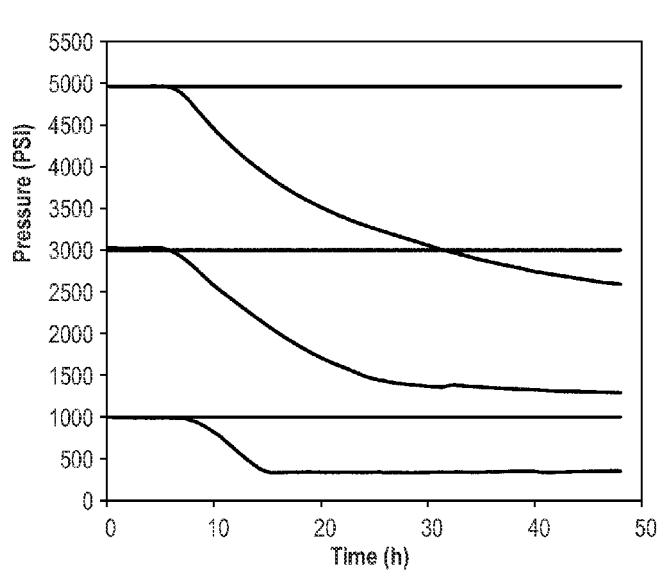
FIGS. 9A and 9B, respectively, show the initial stress state and the pressure-drop (owing to hydration) of cement samples subjected to different curing-pressures.
Figure 9B:
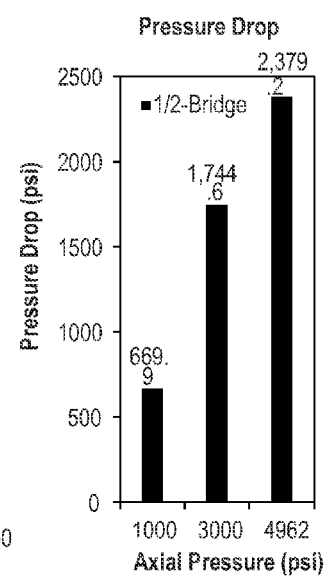
Figure 10:
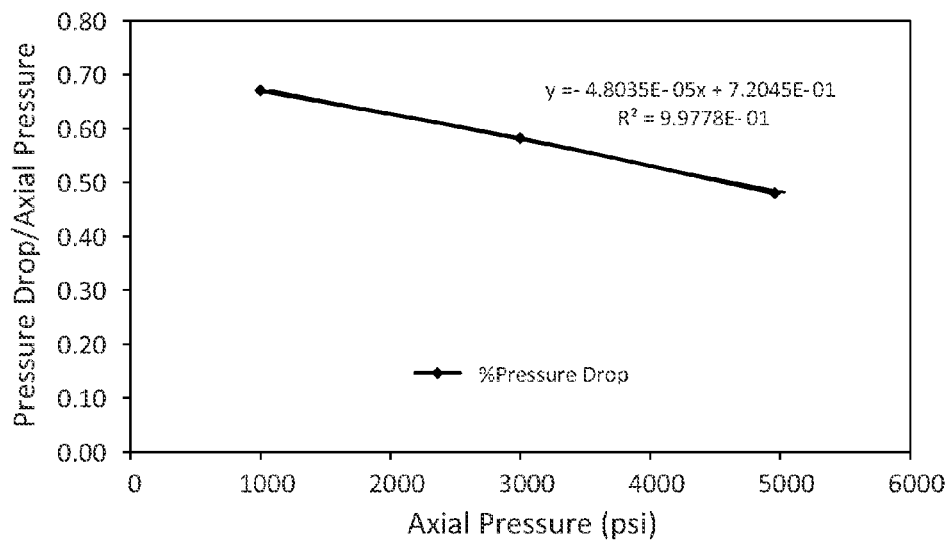
FIG. 10 shows a plot of the relationship between axial curing-pressure and pressure-drop/axial pressure for different curing-pressures.

FIG. 8 compares the change in volume of samples as a function of time for different curing pressures. As expected, the increase in curing pressure resulted in an increment of volumetric shrinkage, FIG. 8. The trends are generally similar to those discussed above with respect to FIG. 5. FIGS. 9A and 9B, respectively, show the influence of curing pressure on the stress state of cement. FIG. 9B reveals that increasing the curing pressure results in greater pressure drop owing to cement hydration. Moreover, FIG. 10 illustrates a linear correlation among pressure drop due to hydration and curing pressure, which is indicative of potential prediction stress state of cement at certain ages.

Figure 11:
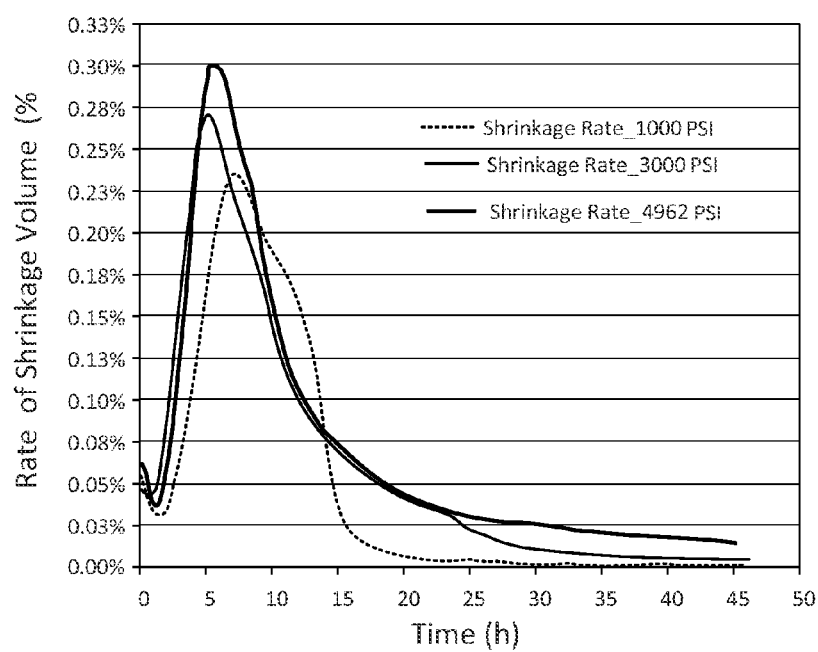
FIG. 11 compares the rate of volume change over time for different applied pressures.

FIG. 11 compares the rate of volume change over time for different applied pressures. Owing to the acceleration effect of the increased pressure causing early static gel strength (SGS) and strength development, it was expected that higher curing pressures would reduce the time at which the maximum shrinkage rate takes place. It is important to notice that the shape of this plot resembles that of heat of hydration, which further confirms the evolution of volumetric shrinkage is hydration dependent, as well as the stress state.

The prototype cell demonstrated the ability to provide accurate results in determining the initial stress state of cement due to cement shrinkage/expansion. However, some embodiments of testing system 100 include modifications that can provide even more precise results and/or more realistically simulate the environment for cement at downhole conditions.

Figure 12A:
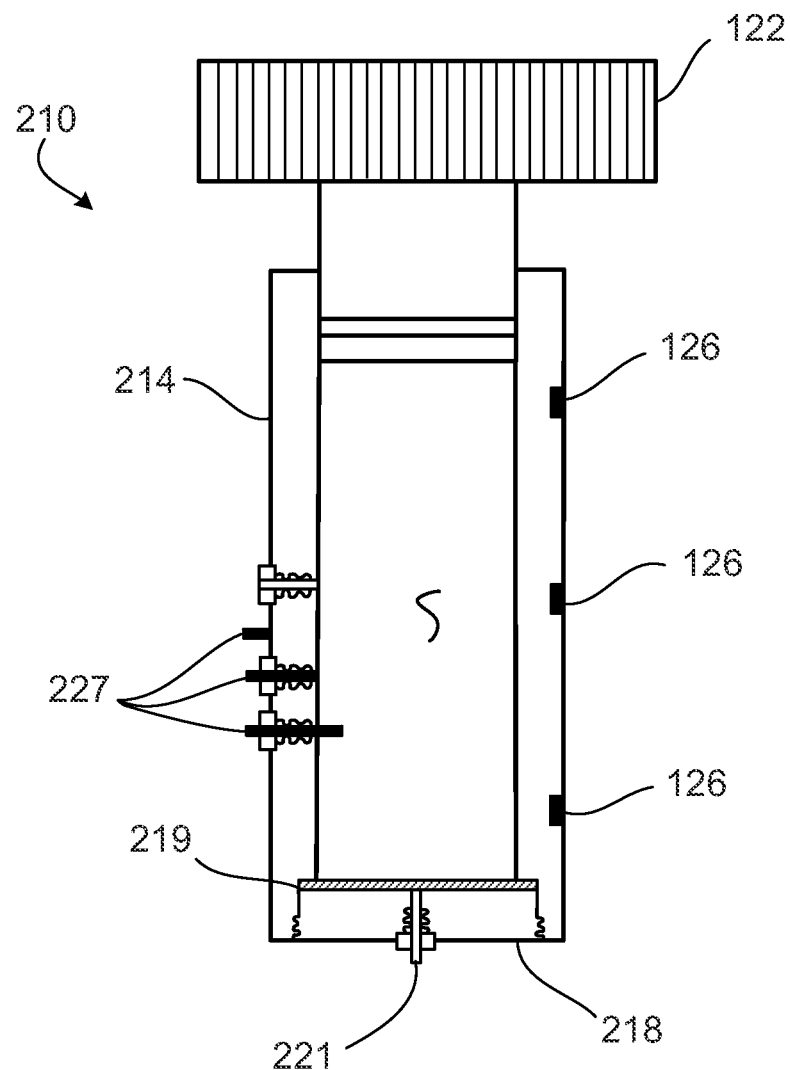
FIG. 12A is a schematic of a testing apparatus.

FIG. 12A is a schematic of a test cell 210. FIGS. 12B-12E are, respectively, an exploded perspective view, an exploded cross-sectional view, an exploded side view, and an assembled side view of the test cell 210 of FIG. 12A. The test cell 210 is substantially similar to the test cell 110 discussed above but includes additional sensors, a temperature control system, a modified bottom piston with a pressure port for application of fluid pressure (for pore pressure simulation), and different size-screens that also enable the application of pore pressure to the sample.

The test cell 210 includes 3 strain gauges distributed along the test chamber 214. The hardening of a cement slurry is not homogenous but rather starts at the bottom of the sample and proceeds upward. Use of multiple strain gauges is anticipated to provide more accurate radial displacement measurements as well as provide insight into the heterogeneity of the hardening process.

The test cell 210 also includes temperature control system with three thermocouples 227 placed to measure temperature at the outer surface of test chamber 214, at the outer surface of the cement sample, and within the cement sample. This allows for heat of hydration monitoring. The temperature control system operates by a Eurotherm controller to achieve downhole temperature conditions based on data from the thermocouples 227. The thermocouples can also be used to monitor the temperature changes of the sample as the cement slurry cures.

The test cell 210 includes an end cap 218 rather than a bottom piston. Various mesh size screens 219 are disposed adjacent the end cap 218. A 320-mesh size screen allows for pore pressure simulation by allowing water to flow through the porosity of the samples and avoid the sample flowing towards the pore pressure fluid source. Additionally, a 60-mesh size screen is employed to provide stability to the 320-mesh screen. Fluid communication with a port 221 is defined extending through the end cap 218. This configuration enables the application of fluid pressure to the cement sample. Either water or oil can be employed for this purpose. Furthermore, an additional pressure transducer can be included to determine the cement pore pressure. A hydraulic pump can be employed as the pore pressure source.

Figure 13A:
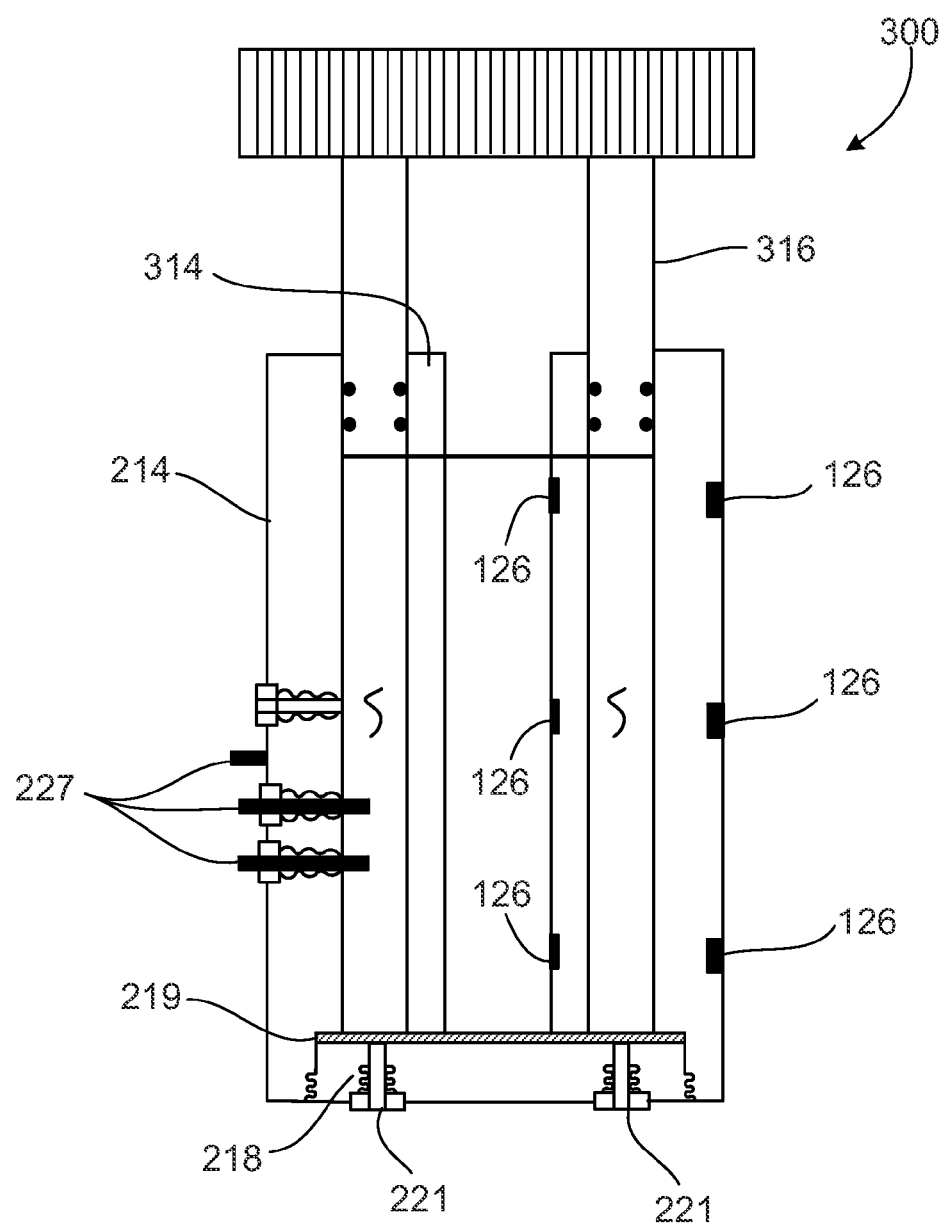
FIG. 13A is a schematic of a testing apparatus.
Figure 13E:
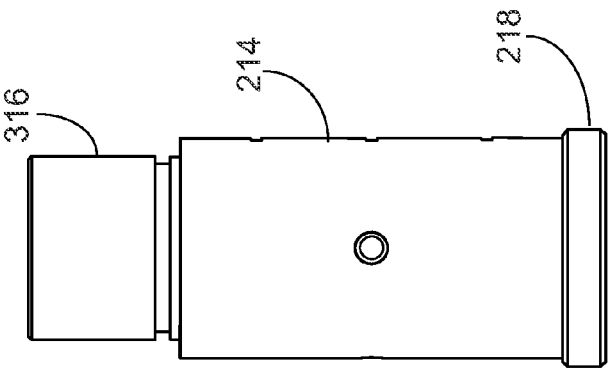
FIGS. 13B-13E are, respectively, an exploded perspective view, an exploded cross-sectional view, an exploded side view, and an assembled side view of the testing apparatus of FIG. 13A.
Figure 13D:
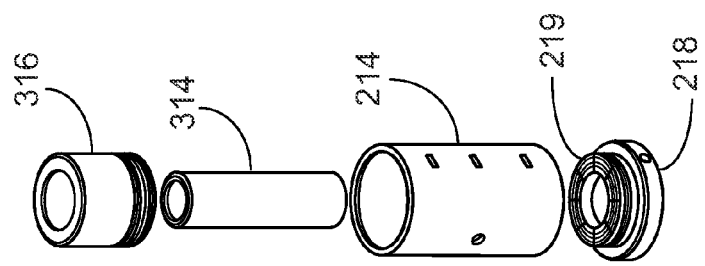
Figure 13C:
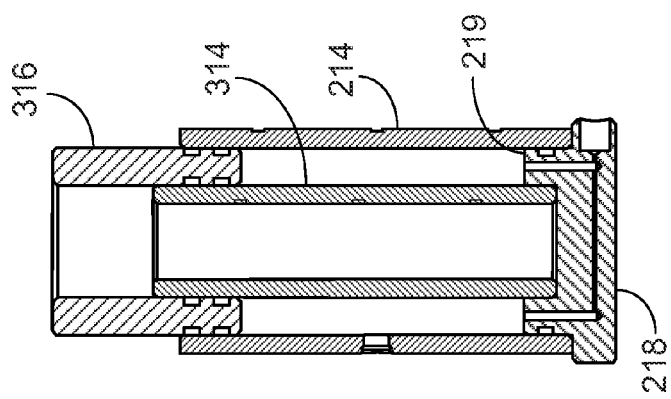
Figure 13B:
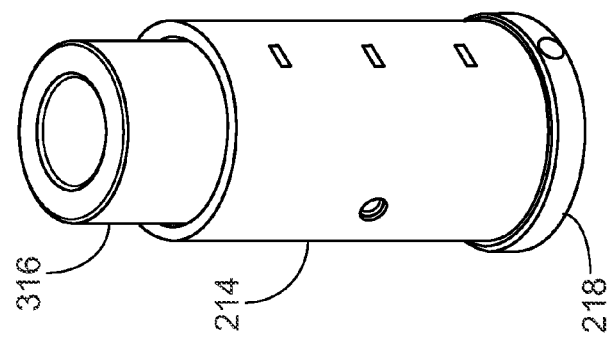

FIG. 13A is a schematic of a testing apparatus. FIGS. 13B-13E are, respectively, an exploded perspective view, a exploded cross-sectional view, an exploded side view, and an assembled side view of the testing apparatus of FIG. 13A. As discussed above, downhole applications for cements include filling the annular space between a well casing and the surrounding formation. Testing system 300 is substantially similar to testing system 200 but has a two-cylinder test cell 310 to simulate the annular systems such as pipe-in-open hole and pipe-in-pipe downhole environments. The test cell 310 includes a hollow top piston 316 sized to fit in the annulus between the test chamber 214 and an inner pipe 314. Three strain gauges 126 are disposed on the inner surface of inner pipe 314. This modified shrinkage/expansion test cell enables simulation of the downhole cement environment including the formation (represented by the external pipe or the top piston), downhole temperature and hydrostatic pressure (controlled by the heat-temperature control system and the top piston, respectively), exposure to external fluids (simulated by the various size mesh screens and application of pore pressure); and the casing (represented by the internal pipe). Furthermore, the weight of fluids above the cement sheath can also be simulated by the load applied to the top piston. The data recorded by inner and outer strain gages can be employed to determine the absolute radial deformation of the cement sample.

Shear and hydraulic bond testing can also be performed with this piece of equipment. Correlating these two parameters to cement hydration will result in a key piece of information to evaluate gas migration considering its direct relationship to hydraulic bond. Furthermore, hydrostatic pressure loss correlation to cement hydration and to the transition period are also achievable with this device and directly related to SGS and therefore to gas migration.

A number of embodiments have been described. Nevertheless, it will be understood that various modifications may be made.

For example, in some embodiments, some cement test cells 110 includes a modified piston 116 that defines a channel that can be used to controllably vent gases as interior spaces of the cement test cell 110 during with a pressurized cement slurry. U.S. Pat. No. 5,869,750 and U.S. Patent Publication Number 2011/0094295 discuss methods and equipment that can be used in preparing and testing a slurry of a cement sample without exposure to ambient pressure conditions. The entire contents of these references are incorporated herein by reference.

In another example, some testing systems 100 incorporate a control pressure mechanism. For example, the control pressure mechanism can be provided using the Instron load frame employed in the prototype system. The control pressure mechanism can also be provided using an added syringe injection pump. The syringe pump approach requires modifying the top piston and adding a top end cap. The modified testing system can be used to develop a relationship between the axial pressure, the pressure applied to the cement by the cylindrical cell, and the strain changes resulted from the volumetric shrinkage.

Accordingly, other embodiments are within the scope of the following claims.

What is claimed is:

1. A method for testing a sample of a fluid mixture that hardens into a solid, the method comprising:
placing the sample of the fluid mixture into a test chamber that provides a ratio of resistance and flexibility to generate a radial deformation of the sample;
applying a pressure to the sample in the test chamber that is different than ambient air pressure around the test chamber;
monitoring axial dimensions and radial dimensions of the sample during the application of pressure
identifying an initiation of gelling and hardening of the sample based on a start of changes to the radial dimensions of the sample independent of a start of changes to the axial dimensions of the sample.

2. The method of claim 1, further comprising determining an initial stress state of the sample by calculating a stress state of the sample at or after the identified initiation of gelling of the sample.

3. The method of claim 1, further comprising controlling a temperature of the test chamber.

4. The method of claim 1, wherein the test chamber comprises an annular portion.

5. The method of claim 1, further comprising developing a calibrated stress-strain relationship for the test chamber by pressurizing the test chamber in the absence of a sample and recording pressure and strain.

6. The method of claim 1, further comprising applying conditions in the test chamber after the sample cures to simulate well operation events.

7. The method of claim 1, further comprising applying a first pressure to bottom surfaces of the sample and a different second pressure to top surfaces of the sample.

8. The method of claim 1, further comprising measuring strain at multiple locations distributed axially along the test chamber.

9. The method of claim 8, further comprising assessing heterogeneity of gelling and hardening of the sample based on differences in the strain measured at the multiple locations distributed axially along the test chamber.

10. The method of claim 1, further comprising performing shear and/or hydraulic bond testing on the sample in the test chamber.

11. The method of claim 2, wherein the initial stress state defines a distance that the sample is from failure or a stress state of the sample prior to an applied load after the identified initiation of gelling of the sample.

12. A method for testing a sample of a fluid mixture that hardens into a solid, the method comprising:
    placing the sample of the fluid mixture into a test chamber that provides a ratio of resistance and flexibility to generate a radial deformation of the sample;
    monitoring an axial dimension and a radial dimension of the sample during an application of pressure to the sample; and
    identifying an initial stress state of the sample of the cement at or after an initiation of gelling and hardening of the sample based on a change to the radial dimension of the sample independent of a change to the axial dimension of the sample.

13. The method of claim 12, further comprising applying a pressure to the sample in the test chamber that is different than ambient air pressure around the test chamber.

14. The method of claim 12, further comprising monitoring axial dimensions and radial dimensions of the sample over a particular time duration.

15. The method of claim 12, further comprising developing a calibrated stress-strain relationship for the test chamber by pressurizing the test chamber in the absence of a sample and recording pressure and strain.

16. The method of claim 12, further comprising applying a first pressure to bottom surfaces of the sample and a different second pressure to top surfaces of the sample.

17. The method of claim 12, further comprising applying conditions in the test chamber after the sample cures to simulate well operation events.

18. A method for assessing a cement, the method comprising:
    monitoring an axial dimension and a radial dimension of a sample of the cement during an application of pressure to the sample in a test chamber;
    identifying a stress state of a sample of the cement at an initiation of gelling and hardening of the sample based on a change to the radial dimension independent of a change to the axial dimension;
    using the identified stress state of the sample of the cement as an initial stress state parameter input into a computer well model; and
    performing well life modeling of the of the cement using the computer well model.

19. The method of claim 18, wherein performing well life modeling comprises simulating at least one of cementing, pressure testing, swabbing, hydraulic fracturing, and production.

20. The method of claim 18, further comprising simulating application of stresses to a virtual cement sheath in the computer well model to estimate a distance to failure for the cement under different conditions.

21. The method of claim 12, wherein the initial stress state defines a distance that the sample is from failure or a stress state of the sample prior to an applied load after the identified initiation of gelling of the sample.

* * * * *

UNITED STATES PATENT AND TRADEMARK OFFICE
CERTIFICATE OF CORRECTION

| | | |
|---|---|---|
| PATENT NO. | : 8,794,078 B2 | Page 1 of 1 |
| APPLICATION NO. | : 13/542011 | |
| DATED | : August 5, 2014 | |
| INVENTOR(S) | : Robert Phillip Darbe et al. | |

It is certified that error appears in the above-identified patent and that said Letters Patent is hereby corrected as shown below:

In the Claims

Column 12, Line 19, replace "of the of the" with -- of the --

Signed and Sealed this
Eleventh Day of November, 2014

Michelle K. Lee
*Deputy Director of the United States Patent and Trademark Office*